United States Patent [19]
Vcelka et al.

[11] 4,456,009
[45] Jun. 26, 1984

[54] INTRAVENOUS PUMP CHAMBER ASSEMBLY

[75] Inventors: John L. Vcelka, Zion; Jay J. Pisik, Deerfield; Clive P. Hohberger, Glencoe, all of Ill.

[73] Assignee: Abbott Laboratories, North Chicago, Ill.

[21] Appl. No.: 164,434

[22] Filed: Jun. 30, 1980

[51] Int. Cl.$^3$ ............................................. A24D 1/18
[52] U.S. Cl. ...................................... 604/152; 417/474; 604/250; 604/251
[58] Field of Search .......... 128/214 F, 273, DIG. 12, 128/675; 417/474; 406/151–153, 123, 246, 67

[56] References Cited

U.S. PATENT DOCUMENTS

| | | | |
|---|---|---|---|
| 3,811,800 | 5/1974 | Shill | 128/153 |
| 4,072,056 | 2/1978 | Lee | 128/675 |
| 4,079,736 | 3/1978 | Lundquist | 128/214 R |
| 4,126,132 | 11/1978 | Portner et al. | 128/153 |
| 4,199,307 | 4/1980 | Jassawalla | 417/474 |
| 4,217,993 | 8/1980 | Jess | 128/153 |
| 4,256,437 | 3/1981 | Brown | 128/13 |
| 4,273,121 | 6/1981 | Jassawalla | 128/153 |
| 4,277,226 | 7/1981 | Archibald | 128/153 |

OTHER PUBLICATIONS

U.S. patent application Ser. No. 06/34,826.

Primary Examiner—V. Millin
Attorney, Agent, or Firm—Neil E. Hamilton

[57] ABSTRACT

A disposable intravenous pump chamber assembly for an intravenous administration set which substantially reduces the problem of air bubble entrapment so that the amount of intravenous fluid delivered is effected in an accurate manner. The pump chamber assembly is specifically constructed to be utilized in conjunction with a diaphragm-type pump with external valving. The pump chamber cassette is held in the pump in a unique manner and includes a porting and fluid delivery arrangement which reduces the problem of air entrapment in the pump chamber.

18 Claims, 8 Drawing Figures

INTRAVENOUS PUMP CHAMBER ASSEMBLY

BACKGROUND OF THE INVENTION

This invention relates to a pump chamber assembly for an intravenous pump of the diaphragm-type. More particularly, this invention relates to a pump chamber cassette for an intravenous pump wherein the pump chamber is constructed in a manner with inlet and outlet ports and is retained in a pump in a position so that air bubble entrapment is substantially eliminated.

Pump chambers of the type concerned with in this invention are described in U.S. Pat. No. 4,199,307. In this particular patent, a specific configuration of a cassette is described for use in a peristaltic-type pump. In U.S. Ser. No. 34,826 filed Mar. 30, 1979 by the assignee of this application, an intravenous pump chamber is illustrated for use with a diaphragm-type pump wherein a diaphragm member is positioned on a pump chamber housing in a manner specifically suitable for large scale production. U.S. Pat. No. 4,079,736 illustrates another version of an I.V. pump cassette which is indicated therein by the numeral 17.

In utilizing diaphragm-type pumps with the types of pump chamber cassettes previously described, a problem arises with the entrapment of air in the pump chamber. When this occurs, accuracy is sacrificed in that air can accumulate in the pump chamber and thus an accurate amount of fluid will not be pumped from the chamber.

It is an advantage of the present invention to provide an intravenous pump chamber cassette which will afford accurate delivery of I.V. fluids. Other advantages are a pump chamber cassette which substantially reduces the accumulation of air bubbles therein; an intravenous pump chamber cassette which includes orientation means to assure that the pump chamber is positioned in the pump in a predetermined manner; a pump chamber assembly which is held in the pump in a predetermined position so as to cause any air bubbles to migrate to the outlet passage; a pump chamber cassette which has means in conjunction with the orientation means to activate the pump when it is positioned therein; a pump chamber assembly which is formed as an integral part of an I.V. administration set and is fabricated at low cost.

SUMMARY OF THE INVENTION

The foregoing advantages are accomplished and the shortcomings of the prior art are overcome by the present pump chamber cassette for a diaphragm-type pump wherein the chamber includes a base member defining a central cavity portion. A diaphragm member is positioned and fixed over the cavity. A retaining member which defines a central opening to accommodate a plunger member is secured to the base member to accommodate the diaphragm therebetween in a sealing relationship. Inlet and outlet ports extend through the base member and are in fluid communication with the central cavity portion. The inlet and outlet ports are positioned within the confines of the cavity portion to communicate therewith and they are spaced from each other diametrically with the outlet port positioned adjacent the periphery of the cavity. The base member is provided with an air bubbling deterring surface between the inlet and outlet ports. Tubing receiving means are defined by each inlet and outlet port. Fluid inlet and outlet flexible I.V. tubing are secured to the respective receiving means of the inlet and outlet ports.

In a preferred embodiment, the inlet port is positioned below the outlet port and the retaining member includes finger avoidance means in the form of a saw tooth surface. The pump chamber may include a combined orientation and activation means for orientating the base member in a pumping member to activate a reset mechanism in the pumping member. The orientation means utilized in conjunction with the pump chamber serves to assure that the inlet tubing will extend upwardly from the pump chamber and the outlet tubing will extend downwardly therefrom. In this manner, the inlet port of the pump chamber cassette, as it is held in the pump, will be at the bottom of the cassette while the outlet port will be at the top. Also, preferably, the pump chamber assembly is utilized in conjunction with an I.V. pump of the diaphragm-type wherein a mounting member is utilized having a compartment which will accommodate the pump chamber and will position it at an angle in the range of 5° to 10° from the vertical.

BRIEF DESCRIPTION OF THE DRAWINGS

A better understanding of the intravenous pump chamber assembly and its use in an intranvous pump will be accomplished by reference to the drawings wherein.

DESCRIPTION OF THE INVENTION

Figure 1:
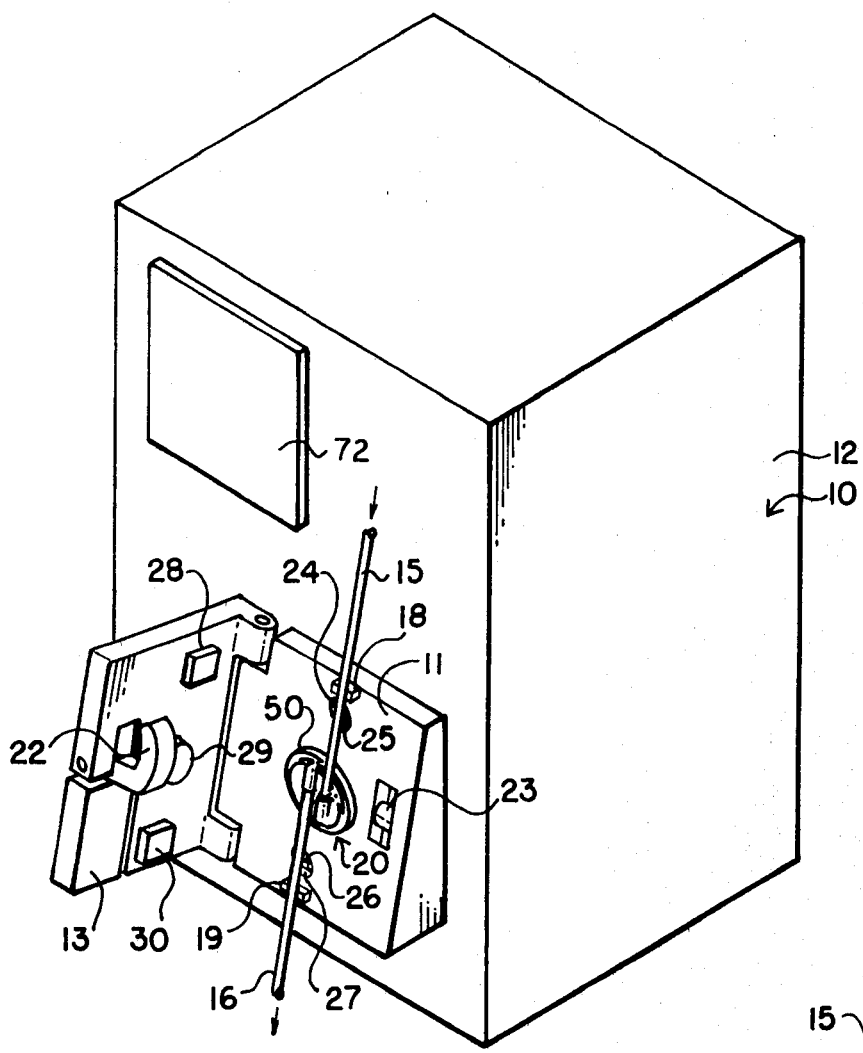
FIG. 1 is a perspective view of a pump of the diaphragm-type with the pump chamber assembly mounted therein.

Proceeding to a detailed description of one embodiment of the present invention, a pump mechanism 10 is shown in FIG. 1 which includes a mounting member 11 with a door is hingedly attached thereto. A pump chamber cassette 20 is partially accommodated in the mounting member with flexible I.V. inlet tubing 15 extending upwardly therefrom and flexible I.V. outlet tubing 16 extending downwardly from the pump chamber. Tube holders 18 and 19 help to secure the tubing to the holder. Door 13 has a door latch 22 which will engage a door catch 23 when the door is closed on the mounting member 11. Two reciprocal contact members 25 and 26 are accommodated in guide passageways 24 and 27 for contact with tubing 15 and 16. Also mounted on door 13 are two anvil surfaces 28 and 30 as well as 29, the purpose of which will be described later.

Figure 2:
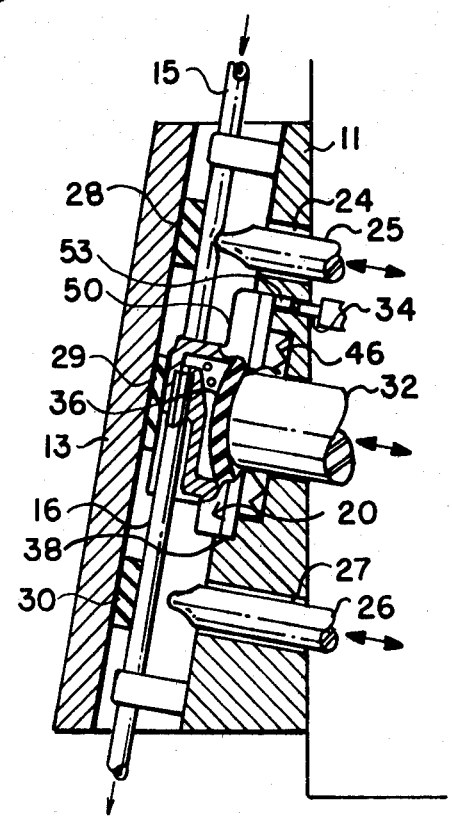
FIG. 2 is a detailed view of the pump chamber assembly as it is mounted in the pump of FIG. 1 with the view shown in vertical section.
Figure 4:
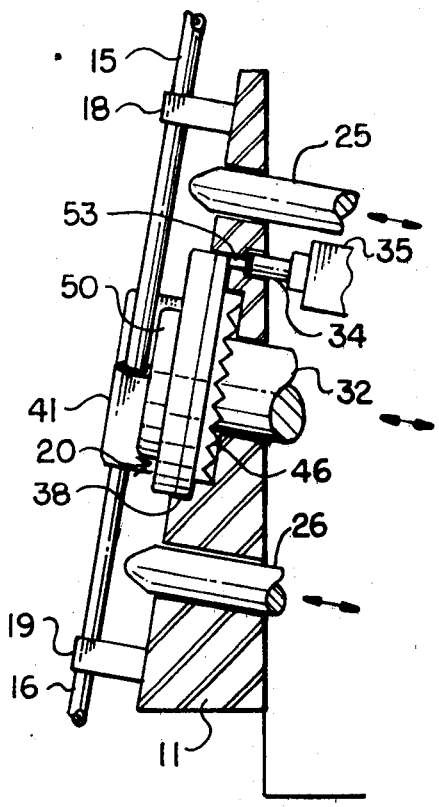
FIG. 4 is a view in vertical section of the pump chamber assembly mounted in the pump as shown in FIG. 3.

The retention of pump chamber cassette 20 in mounting member 11 is best seen in FIGS. 2 and 4. In these figures it will be seen that pump chamber cassette 20 and compartment 38 for accommodating the cassette are positioned so that they are coaxial with the line of travel of plunger member 32 with chamber 20 being centrally contacted thereby. This is afforded through step-like compartment 38 being provided in the mounting member 11 and having the same basic external configuration as the pump chamber 20 to accommodate a portion of base member 50. Positioned adjacent compartment 38 and for contact with a portion of the base member 50 is a switch button 34 which activates switch 35. A projection member 53 extends from base 50 for contact with switch button 34.

Figure 3:
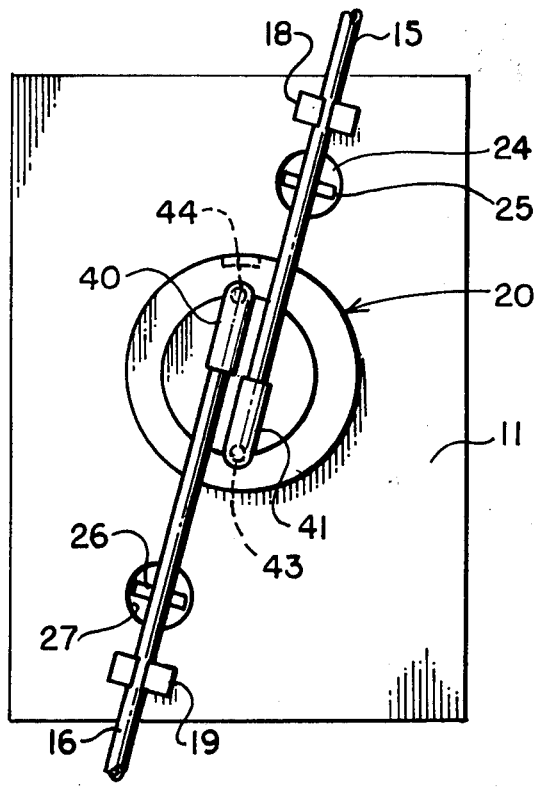
FIG. 3 is a front view of the pump chamber assembly shown in FIG. 1.
Figure 5:
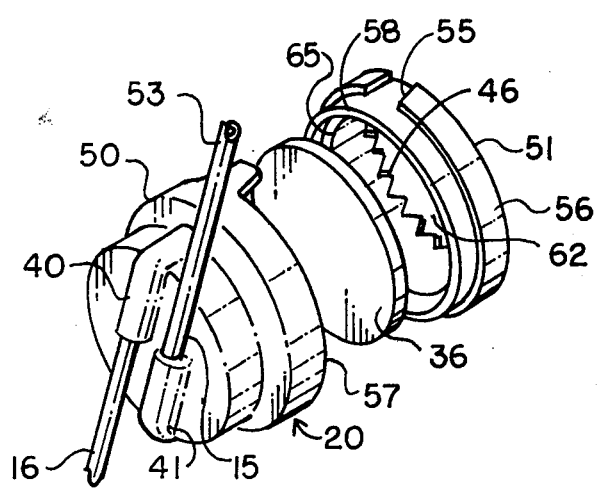
FIG. 5 is an assembly view of the pump chamber cassette.
Figure 6:
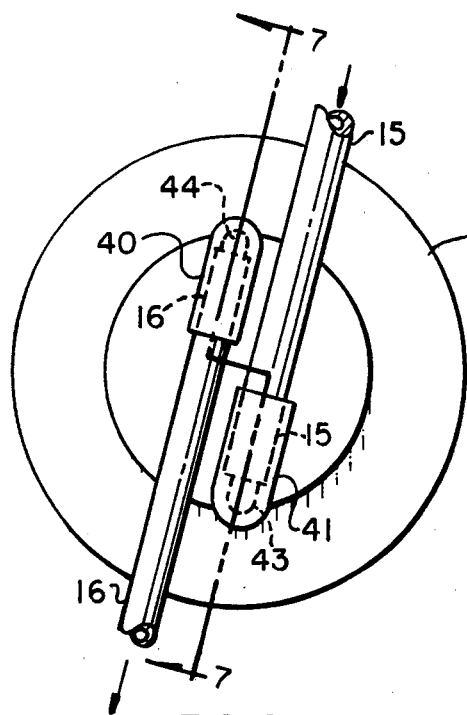
FIG. 6 is an enlarged view of the pump chamber cassette shown in side elevation.
Figure 7:
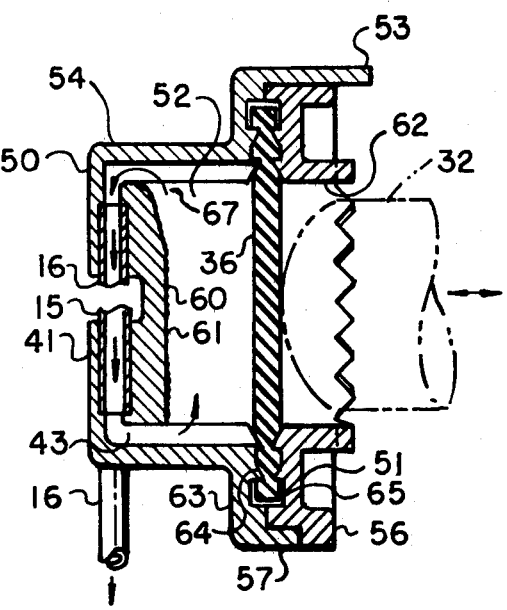
FIG. 7 is a view in vertical section taken along line 7—7 of FIG. 6.

As best indicated in FIGS. 3 and 5, pump chamber 20 has extending from base member 50 opposing outlet and inlet ports 40 and 41 respectively. Outlet port 40 is enlarged to receive outlet tubing 16 and similarly inlet port 41 receives inlet tubing 15. This is also illustrated in FIGS. 6 and 7. Inlet passage 43 and outlet passage 44 communicate with inlet and outlet ports 41 and 40 respectively, as well as to the inside of base member 50 and the cavity 52 provided by annular wall portion 54.

As best seen in FIG. 5, pump chamber cassette 20 includes base member 50 and a retaining member 51 for orientation therewith. A diaphragm 36 in the form of a flat disc is dimensioned to fit between base 50 and retaining member 51. It is frictionally retained therebetween by means of flanges 63 and 65 having barbed surfaces 64. This is best illustrated in FIG. 7. Retaining member 51 has an angular passage 55 on the circumference thereof to accommodate angular projection 53. It will be noted that not only does projection 53 fit into and is accommodated by passage 55, but the projection will extend beyond retaining member 51 as indicated in FIG. 7. The interior of base member 50 includes a wall surface 60 with matting 61 for the purpose of preventing air bubble formation and affording air bubble transmission to the top of the chamber as will be further discussed in the operation. A saw toothed portion 46 extends from retaining member 51 and diaphragm 36 is concentric with cavity 62 for the purpose of deterring finger contact with diaphragm 36. This feature is best illustrated in FIGS. 4 and 5.

Figure 8:
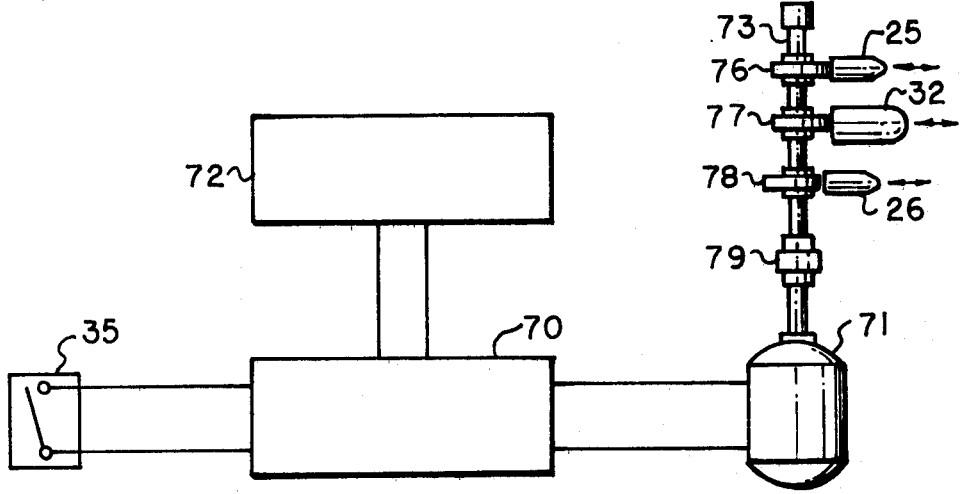
FIG. 8 is a diagrammatic view showing the components employed in activating the pump.

FIG. 8 illustrates the control electronics for activating pump 10 and driving contact members 25 and 26 as well as plunger member 32. It will be appreciated that the following described electronics will be housed inside pump housing 12. Switch 35 will be electrically connected to a microprocessor 70 which in turn is electrically connected to motor 71. A cam shaft 73 with cams 76, 77 and 78 is driven by motor 71 through connection 79. Cam shaft 73 will be oriented with respect to tubing contacts 25, 26 and plunger 32 so that cams 76, 78 and 77 will rotatably engage the respective contacts 25, 26 and plunger 32. The operation mode of microprocessor 70 will be seen on display panel 72 which is operatively joined with the microprocessor. It will be appreciated that the microprocessor can be utilized to activate a reset mechanism for motor 71.

OPERATION

A better understanding of the advantages of the pump 10 and the pump chamber cassette 20 will be had by a description of their operation and fabrication.

Pump chamber cassette 20 will be fabricated in three parts as indicated in FIG. 5. To assemble the pump chamber, diaphragm 36 will be placed between base member 50 and retaining member 51 with projection 53 extending through passage 55. In this position, diaphragm 36 will be frictionally engaged by the barbed surfaces 64 of flanges 63 and 65 with retaining member 51 being sealed to base 50 by means of ultrasonic welding and the overlap of wall section 57 of base 50 over wall section 58 of retaining member 61. This results in a pump chamber cassette 20. The next step in the fabrication will be the placement of inlet tubing 15 and outlet tubing 16 in inlet port 41 and outlet port 40, respectively. The tubing will be retained in the respective ports by solvent bonding. The tubing 15 and 16 connected to the pump chamber cassette 20 results in an assembly herein referred to as an intravenous pump chamber assembly. It will be appreciated that the inlet and outlet tubing will form a portion of an I.V. administration set with inlet tubing 15 being connected to the usual source of I.V. fluid and a drip chamber. Outlet tubing 16 will be connected to an I.V. administration needle.

When it is desired to utilize the pump chamber cassette 20 to deliver I.V. fluid, the usual venipuncture will be made and the source of I.V. fluid supported above pump 10. The door 13 of pump 10 will be opened and the pump chamber assembly placed onto mounting member 11. This is accomplished by placing base member 50 into compartment 38 of mounting member 11. Inlet tubing 15 will be placed into tube holder 18 while outlet tubing 16 is placed in tubing holder 19. Door member 13 will then be closed with door latch 22 engaging door catch 23. This will place anvil surfaces 28 and 30 opposite tubing contact members 25 and 26 and anvil surface 29 opposite plunger member 32. It will be seen that when base member 50 is placed into compartment 38, projecting member 53 will engage switch button 34 to close switch 35. This contact will be maintained by the closing of door 13. The closing of switch 35 will activate motor 71 through microprocessor 70. The particular mode of the microprocessor will be viewed on display 72. Cam operated drive shaft 73 will be rotated by motor 71 to move sliding contact members 25 and 26 as well as plunger 32 in the usual peristaltic pattern for pumping purposes. For example, in an open position, slide member 26 will be moved against outlet tubing 16 and anvil surface 30 with plunger 32 and slide contact member 25 retracted. In a pumping mode, slide member 26 will then be retracted, slide member 25 will be extended forward to press inlet tubing 15 against anvil surface 28 and plunger 32 will be moved to a forward position to move into central cavity 62 of retainer 51 to thereby reduce the volume of cavity 52. This causes liquid to flow from the pump cavity to outlet tubing 16.

It will be noted that when pump chamber cassette 20 was placed in mounting member 11 that inlet port 41 will be placed downwardly of the pump, whereas outlet port 40 will be at the top. In addition, as best seen in FIGS. 2 and 4, the pump chamber cassette will be held in mounting member 51 at an angle of 7°. The positioning of the inlet passage and the outlet passage, the angle of inclination of the pump chamber cassette 20, as well as the utilization of the matting 61 in wall surface 60 of base member 50 substantially assures that any air which enters through inlet tubing 15 will be directed to the top of base member 50 and will flow out through outlet port 40 when plunger 32 contacts diaphragm 36 during its compression stroke. The movement of the fluid as well as the air bubbles through chamber cavity 52 is illustrated by directional arrows 67. By placing the inlet and outlet passages within the confines of said cavity portion and the outlet orifice at the top of pump chamber cassette 20, as well as inclining the chamber at the specified angle, any air bubbles are directed to the outlet port so that they will be expected from the cavity 52 during each compression stroke of plunger 32.

It will be appreciated that projection 53 on base 50 affords not only a reset and start mechanism for the pump 10 but also serves as an orientation means so that outlet port 40 is positioned at the top of pump chamber cassette 20 as it is disposed adjacent thereto. If desired and to assure that the operator will place projection 53 in contact with switch button 34, suitable indicia could be indicated on mounting member 11. When a different I.V. administration is to be effected through pump 10 all that is required is the pump chamber assembly be removed from compartment 38 and the tubing 15 and 16 from their respective holders by a slight pulling force.

In the previous description of the operation, an angle of 7° was indicated as being important for the placement of the pump chamber cassette in the retaining member. This angle can vary to some extent and could range from 5° to 10°. Also, while a matting such as 61 was indicated for chamber wall 60, any roughening of the surface such as by modifying the mold which makes the thermoplastic part by grit blasting, electric discharge machining (EDM), chemical etching, broaching or any other machining process could afford the same desired effect. Further, while the pump chamber cassette 20 is substantially round in configuration, it will be appreciated that any geometric configuration could be employed with a complementary configuration of a compartment being provided in retaining member 11 and a portion of the pump chamber cassette being extended so as to activate a switch button. Similarly, diaphragm 36 is fabricated in the form of a flat disc. Any configuration of a diaphragm could be utilized in the pump chamber of this invention such as that of a "top hat."

The preferred materials for fabricating base member 50 and retaining member 51 are rigid polyvinyl chloride or polycarbonate. However, other materials such as polyester or styrene acrylonitrile could be employed. The preferred material for fabricating diaphragm 36 is silicone. However, other elastic materials such as polyurethane or natural rubber could be utilized.

It will thus be seen that through the present invention there is provided a novel pump chamber cassette and I.V. pump which affords for accurate delivery of I.V. fluids in a pump of the diaphragm-type as well as actuation of the pump. Any air which may be delivered to the pump chamber will not become entrapped but will be delivered through the outlet tubing by a unique positioning and fabrication of the pump chamber cassette. The pump chamber assembly can be fabricated from low cost materials and accordingly, is disposable. The pump chamber cassette can be fabricated in a manner using standard tooling and without the need for special materials or component parts.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

We claim:

1. An intravenous pump chamber assembly for an intravenous pump comprising:
    a base member defining a central cavity portion;
    a diaphragm member positioned over said cavity portion;
    a retaining member defining a central opening to accommodate a plunger member, said base member and retaining member constructed and arranged to accommodate said diaphragm therebetween in a sealing relationship;
    inlet and outlet ports defining inlet and outlet passages extending through said base member and in fluid communication with said central cavity portion, said inlet and outlet ports being positioned within the confines of said cavity portion to communicate with said central cavity portion and spaced from each other with said outlet port positioned adjacent the periphery of said cavity, said base member presenting a wall defining an air bubble deterring surface between said inlet and outlet ports;
    tubing receiving means defined by said inlet and outlet ports; and
    inlet and outlet flexible I.V. tubing in fluid-tight communication with said respective inlet and outlet ports.

2. The intravenous pump chamber assembly as defined in claim 1 wherein said inlet port is positioned diametrically opposite from said outlet port.

3. The intravenous pump chamber assembly as defined in claim 2 wherein said pump chamber includes a combined orientation and activation means for orientating said base member in a pumping member and activating a reset mechanism in said pumping member.

4. The intravenous pump chamber assembly as defined in claim 3 wherein said orientation and activating means is defined by a projecting member extending from said pump chamber, said projecting member positioned adjacent said outlet port and extending in a direction outwardly therefrom.

5. The intravenous pump chamber assembly as defined in claim 4 wherein said retaining member includes a passage to accommodate a portion of said projecting member.

6. The intravenous pump chamber assembly as defined in claim 1 wherein said retaining member further includes finger avoidance means operatively positioned adjacent said central opening.

7. The intravenous pump chamber assembly as defined in claim 6 wherein said finger avoidance means is defined by a saw-tooth surface.

8. The intravenous pump chamber assembly as defined in claim 1 wherein said diaphragm member comprises a substantially flat disc and is held in part between said base and retaining members by means of frictional engaging means.

9. The intravenous pump chamber assembly as defined in claim 1 wherein said bubble deterring surface is defined by a matting surface.

10. An intravenous pump of the diaphragm-type comprising:
    a mounting member;
    first and second contact members;
    a plunger member operatively positioned between said first and second contact members;
    means constructed and arranged to move said first and second contact members and said plunger member through said mounting member in a reciprocal manner;
    a base member including a wall portion defining a central cavity portion;
    a diaphragm member positioned over said cavity portion;

a retaining member defining a central opening to accommodate said plunger member; said base member and retaining member constructed and arranged to accommodate said diaphragm therebetween in a sealing relationship, said base, diaphragm and retaining members comprising a pump chamber cassette;

inlet and outlet ports defining inlet and outlet passages extending through said base member and in fluid communication with said central cavity portion; said inlet and outlet ports being positioned within the confines of said cavity portion to communicate with said central cavity portion and spaced from each other with said outlet port positioned adjacent the periphery of said cavity and at the top of said cassette, said base member presenting an air bubble deterring surface between said inlet and outlet ports;

tubing receiving means defined by said inlet and outlet ports;

inlet and outlet flexible I.V. tubing in fluid-tight communication with said respective inlet and outlet ports;

a compartment defined by said mounting member and positioned coaxially with the line of travel of said plunger member, said compartment having substantially the same geometrical configuration as said base member to accommodate a portion of said base member therein, said mounting member constructed and arranged to position said pump chamber cassette in said compartment at an angle in the range of about 5° to 10° from the vertical;

tubing holding means operatively associated with said mounting member to position said tubing for contact with said first and second contact members; and a closure member operatively associated with said mounting member presenting anvil surfaces for said contact members and said plunger member.

11. The intravenous pump as defined in claim 10 wherein said closure member is a door member.

12. The intravenous pump as defined in claim 11 wherein base member is held in said compartment at an angle of 7°.

13. The intravenous pump as defined in claim 10 further including a switch member positioned adjacent said compartment for contact with a portion of said pump chamber cassette when said cassette is placed in said compartment and will be held in contact with said switch member by means of said closure member.

14. The intravenous pump as defined in claim 10 wherein said inlet port is positioned diametrically opposite from said outlet port and said tubing holding means is arranged to position said inlet tubing at the top of said mounting member and said outlet tubing at the bottom thereof with said inlet port positioned below said outlet port.

15. The intravenous pump as defined in claim 14 wherein said retaining member further includes finger avoidance means operatively positioned adjacent said central opening.

16. The intravenous pump as defined in claim 10 wherein said pump chamber includes a combined orientation and actuation means for orientating said base member in said compartment of said mounting member.

17. The intravenous pump as defined in claim 16 wherein said actuation means is defined by a projecting member extending from said pump chamber cassette, said projecting member positioned adjacent said outlet port and extending in a direction outwardly therefrom.

18. The intravenous pump as defined in claim 17 wherein said diaphragm member comprises a substantially flat disc and is held in part between said base and retaining members by means of frictional engaging means.

* * * * *